(12) United States Patent
DeVille (10) Patent No.: US 10,219,820 B2
(45) Date of Patent: Mar. 5, 2019

(54) SURGICAL COMPACTOR AND EXTRACTOR (71) Applicant: Ronald Gene DeVille, Shreveport, LA (US)

(72) Inventor: Ronald Gene DeVille, Shreveport, LA (US)

(*) Notice: Subject to any disclaimer, the term of this patent is extended or adjusted under 35 U.S.C. 154(b) by 618 days.

(21) Appl. No.: 14/872,400

(22) Filed: Oct. 1, 2015

(65) Prior Publication Data

US 2016/0095612 A1 Apr. 7, 2016

Related U.S. Application Data

(60) Provisional application No. 62/058,147, filed on Oct. 1, 2014.

(51) Int. Cl.
*A61B 17/32* (2006.01)
*A61B 17/00* (2006.01)
*A61B 17/3205* (2006.01)
*A61B 17/22* (2006.01)
A61B 17/42 (2006.01)

(52) U.S. Cl.
CPC .. *A61B 17/32002* (2013.01); *A61B 17/22031* (2013.01); *A61B 17/3205* (2013.01); *A61B 2017/00278* (2013.01); *A61B 2017/00287* (2013.01); *A61B 2017/320024* (2013.01); *A61B 2017/320032* (2013.01); *A61B 2017/320064* (2013.01); *A61B 2017/4216* (2013.01)

(58) Field of Classification Search
CPC ........ A61B 17/32002; A61B 17/22031; A61B 17/3205; A61B 2017/4216; A61B 2017/320032; A61B 2017/00278; A61B 2017/320064; A61B 2017/320024; A61B 2017/00287

See application file for complete search history.

(56) References Cited

U.S. PATENT DOCUMENTS

| | | | | |
|---|---|---|---|---|
| 4,820,277 A | * | 4/1989 | Norelli | A61M 5/3216 604/192 |
| 6,139,508 A | * | 10/2000 | Simpson | A61B 10/06 600/564 |
| 2010/0152612 A1 | * | 6/2010 | Headley, Jr. | A61B 10/04 600/566 |

* cited by examiner

*Primary Examiner* — Anh T Dang (57) ABSTRACT

A surgical compactor and extractor for intra-abdominal and laparoscopic surgeries includes a compaction mechanism, a suction tubing, and a suction mechanism. The compaction mechanism has an expandable isolation chamber that is operable between a closed configuration and an open configuration via an actuation mechanism that is either mechanical or pneumatic. The expandable isolation chamber is toggled to the open configuration in order to encompass tissue within a patient's body and then toggled to the closed configuration in order to compact the tissue and remove the tissue from the patient. The suction tubing has an evacuation conduit that traverses along a flexible body and is used in conjunction with the suction mechanism to remove fluid and particulate matter as the tissue is compacted. The suction mechanism includes a vacuum unit to create a pressure differential and a reservoir to collect the fluid and particulate matter.

11 Claims, 10 Drawing Sheets

SURGICAL COMPACTOR AND EXTRACTOR

The current application claims a priority to the U.S. Provisional Patent application Ser. No. 62/058,147 filed on Oct. 1, 2014.

FIELD OF THE INVENTION

The present invention relates generally to intra-abdominal and laparoscopic surgery methods. More specifically, the present invention is a surgical compactor and extractor for use in surgical procedures such as hysterectomies and prostatectomies.

BACKGROUND OF THE INVENTION

A hysterectomy is the removal of a woman's uterus. Reasons for a hysterectomy may include medical issues including uterine fibroids, uterine prolapse, cancer of the uterus, cervix, or ovaries, endometriosis, abnormal vaginal bleeding, chronic pelvic pain, and adenomyosis. Hysterectomies have been made safer and less intrusive by the development of the laparoscopic hysterectomy. In this surgery, a tube with a lighted camera, and surgical tools are inserted through cuts in the belly. The surgeon operates, monitoring the procedure through video. This enables smaller incisions to be made, and provides for a less invasive surgery with a shorter recovery time. However, this operating method does have some associated problems. For one, the trans-vaginal removal of the uterus may not be possible depending on the relative sizes of the patient's uterus and vaginal introits. In these cases, surgeons have sometimes opted to use a morcellator to mince the organs before removal. However, use of power morcellators has been linked to the spread of sarcoma. Accordingly, the Food and Drug Administration has officially discouraged the use of the laparoscopic power morcellators in hysterectomies. Some methods have been developed to increase the safety of morcellator use, including patented technologies for bags which enclose the uterus. But these methods leave much to be desired. An ideal method would be to somehow reduce the size of the uterus in cases to make it removable transvaginally without morcellation.

Therefore it is the object of the present invention to put forth a device which encloses and compresses the uterus, ovaries, and fallopian tubes, permitting their removal through the vagina following a laparoscopic hysterectomy. The present invention includes a compaction mechanism that is terminally connected to a suction tubing. The compaction mechanism includes an expandable isolation chamber that can be toggled between a closed configuration and an open configuration via an actuation mechanism. In the closed configuration, the expandable isolation chamber is small enough to fit into the vaginal introits of average or smaller than average dimension. When in the open configuration, the expandable isolation chamber is able to surround a uterus, ovaries, and fallopian tubes of average or larger than average dimension. The suction tubing allows fluid and particulate matter to be removed as the uterus is compacted within the expandable isolation chamber.

DETAIL DESCRIPTIONS OF THE INVENTION

All illustrations of the drawings are for the purpose of describing selected versions of the present invention and are not intended to limit the scope of the present invention.

The present invention is a surgical compactor and extractor for intra-abdominal and laparoscopic surgeries. In the preferred embodiment, the present invention is designed to perform a hysterectomy, wherein the present invention may also be designed to remove the cervix, ovaries, or fallopian tubes in addition to the uterus. However, it is possible for the present invention to be configured to perform other intra-abdominal and laparoscopic surgeries such as prostatectomies.

Figure 1:
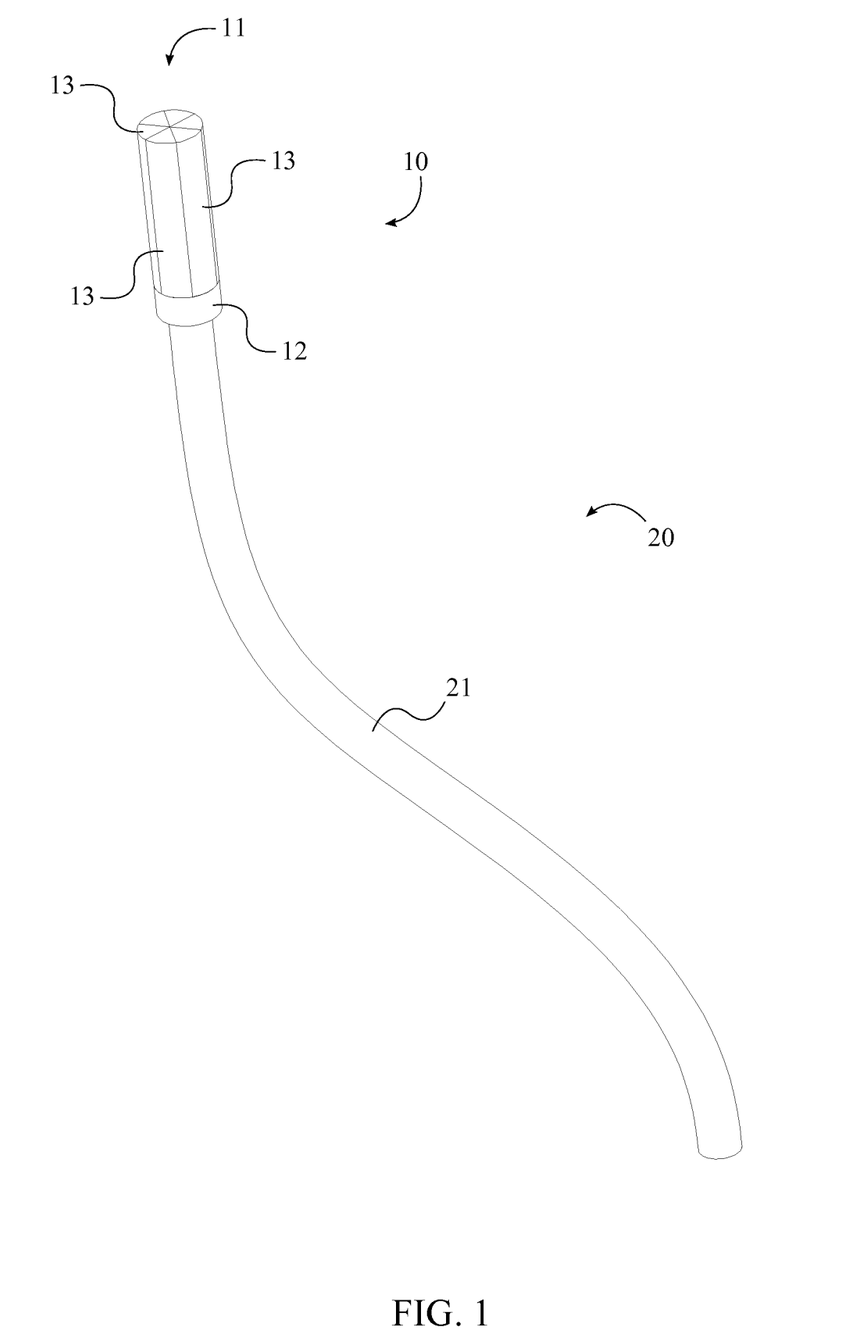
FIG. 1 is a perspective view of the compaction mechanism and the suction tubing, wherein the compaction mechanism is in the closed configuration.
Figure 10:
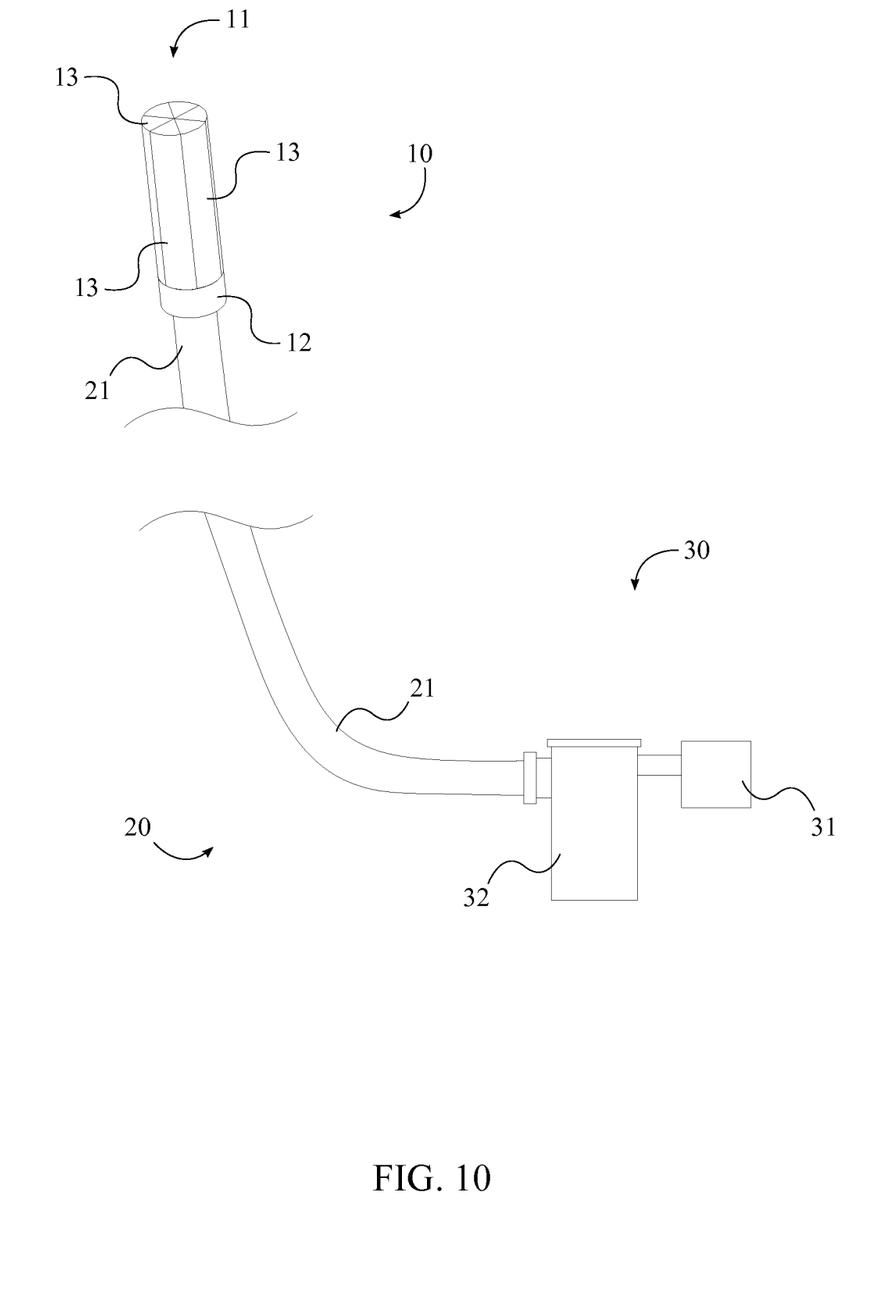
FIG. 10 is a perspective view showing the suction mechanism being terminally attached to the suction tubing opposite the compaction mechanism.

In reference to FIG. 1 and FIG. 10, the surgical compactor and extractor comprises a compaction mechanism 10, a suction tubing 20, and a suction mechanism 30. The compaction mechanism 10 allows a user to target, surround, compact, and remove a sample of tissue within a patient. Meanwhile, the suction tubing 20 and the suction mechanism 30 are used in tandem to remove fluid and particulate matter away from the tissue and the compaction mechanism 10.

Figure 3:
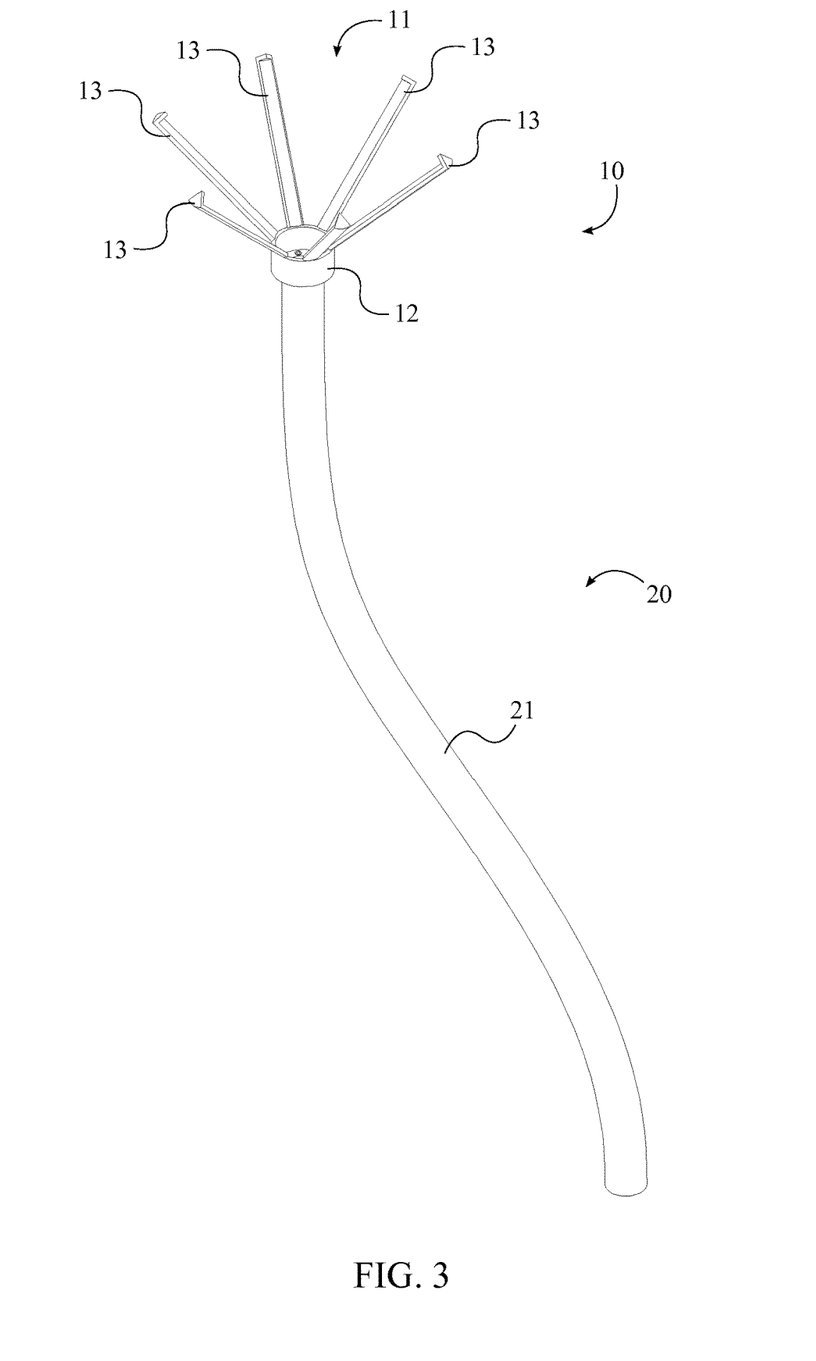
FIG. 3 is a perspective view of the compaction mechanism and the suction tubing, wherein the compaction mechanism is in the open configuration.

The compaction mechanism 10 comprises an expandable isolation chamber 11 and an actuation mechanism. The expandable isolation chamber 11 is a thin walled, hollow structure that is able to open and close in order to surround and encapsulate a uterus (or other tissue). The actuation mechanism is operatively coupled to the expandable isolation chamber 11 and is used to toggle the expandable isolation chamber 11 between a closed configuration, as shown in FIG. 1, and an open configuration, as shown in FIG. 3. In the preferred embodiment of the present invention, the expandable isolation chamber 11 must have a diameter which is small enough to fit into the vaginal introits of average or smaller than average dimension when in the closed configuration; and in the open configuration, the expandable isolation chamber 11 must be able to surround a uterus, ovaries, and fallopian tubes of average or larger than average dimension.

The actuation mechanism can be operatively coupled to the expandable isolation chamber 11 and function in a number of different ways depending on the embodiment of the present invention. In one embodiment of the present invention, the compactor mechanism is mechanically operated, wherein the actuation mechanism comprises components to mechanically open and close the expandable isolation chamber 11. In another embodiment of the present invention, the compactor mechanism is pneumatically operated, wherein the actuation mechanism comprises components to pneumatically open and close the expandable isolation chamber 11.

Figure 2:
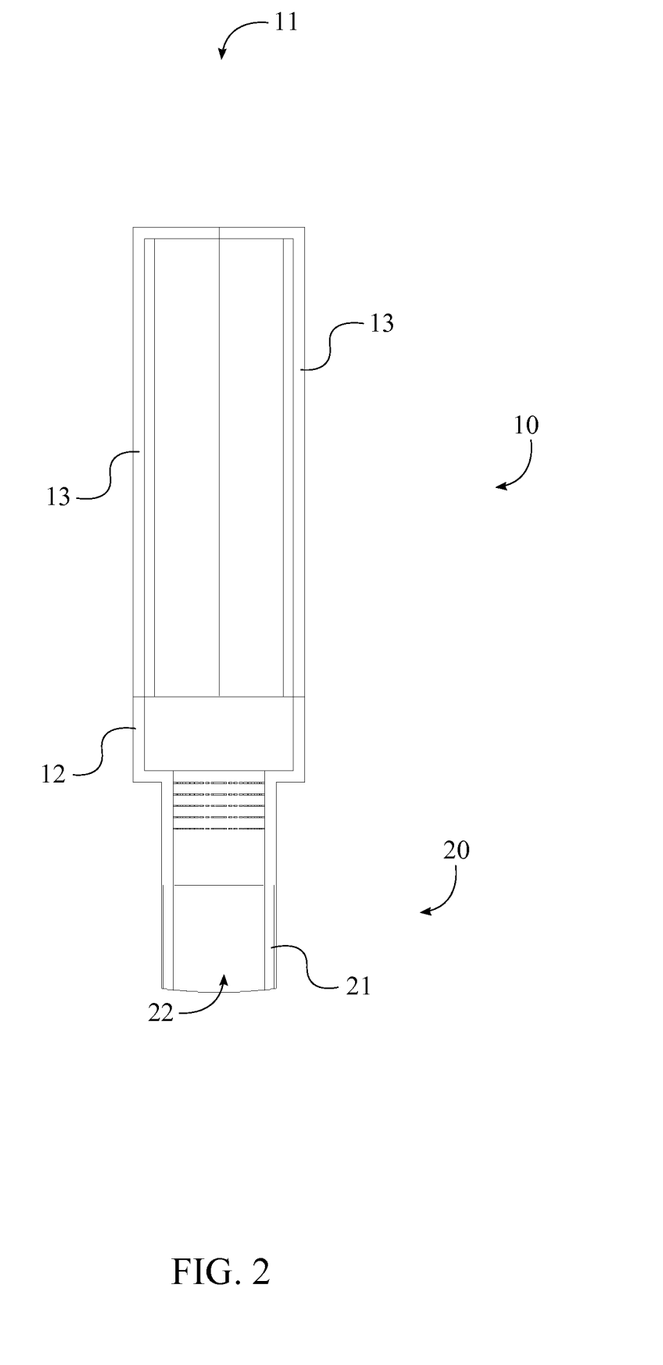
FIG. 2 is a side sectional view of the compaction mechanism and the suction tubing, wherein the compaction mechanism is in the closed configuration.
Figure 9:
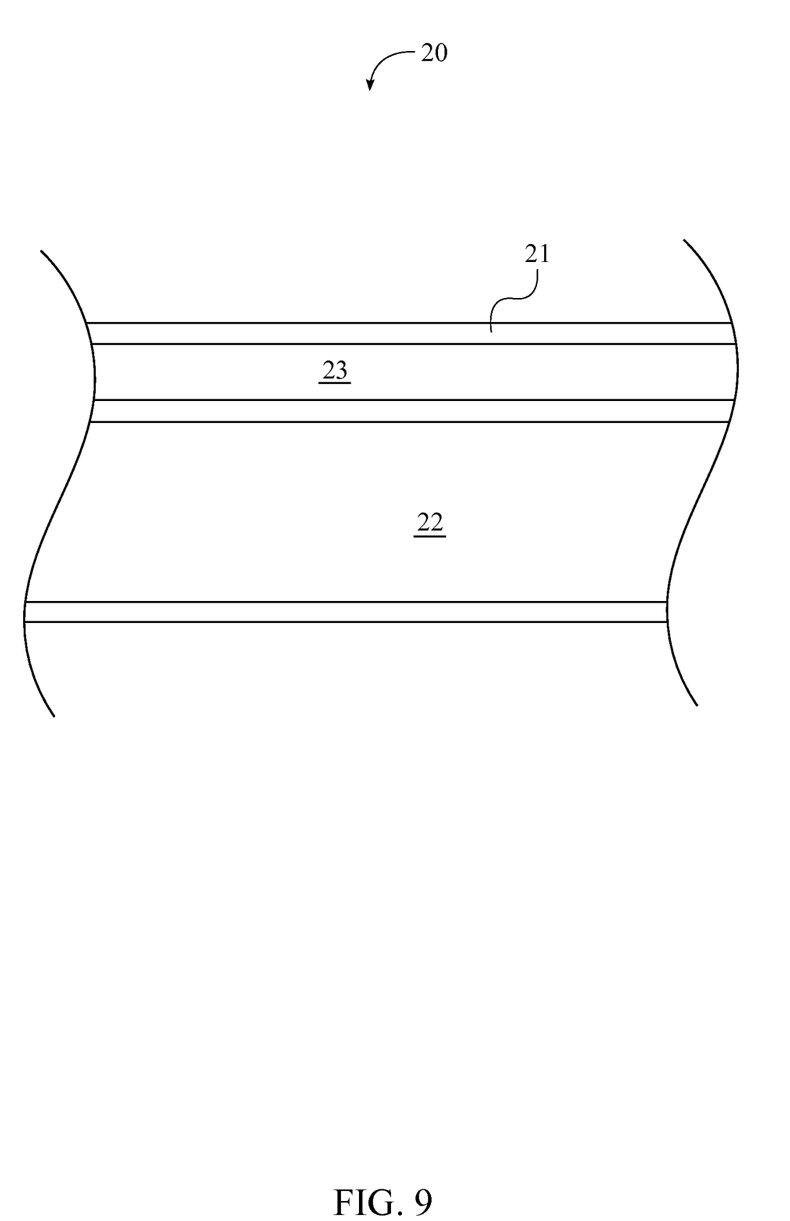
FIG. 9 is a side sectional view of the suction tubing showing the evacuation conduit and the wiring conduit traversing through the flexible body.

In reference to FIG. 2 and FIG. 9, the suction tubing 20 comprises a flexible body 21 and an evacuation conduit 22, wherein the evacuation conduit 22 is positioned along the flexible body 21 and longitudinally traverses through the flexible body 21. The expandable isolation chamber 11 is terminally connected to the flexible body 21, wherein the expandable isolation chamber 11 is first inserted into the patient. The user can then navigate the expandable isolation chamber 11 internally through the patient by manipulating the flexible body 21 external of the patient. For example, during a hysterectomy, the flexible body 21 extends transvaginally from the patient allowing the user to manipulate the position of the expandable isolation chamber 11.

Once the expandable isolation chamber 11 is positioned within the desired location, the actuation mechanism is engaged to toggle the expandable isolation chamber 11 into the open configuration in order to surround the tissue. The actuation mechanism is then engaged again to toggle the expandable isolation chamber 11 into the closed configuration, compacting the tissue. Meanwhile the fluid and particulate matter are removed via the evacuation conduit 22 and the suction mechanism 30.

In reference to FIG. 10, the suction mechanism 30 is attached to the flexible body 21 opposite the compaction mechanism 10 and comprises a vacuum unit 31. The vacuum unit 31 is an air blower or similar mechanism that is attached to the flexible body 21 and is used to expel air from the evacuation conduit 22, thus creating a pressure differential between opposing ends of the evacuation conduit 22 to draw fluid and particulate matter through the evacuation conduit 22. As such, both the expandable isolation chamber 11 and the vacuum unit 31 are in fluid communication with the evacuation conduit 22. When the expandable isolation chamber 11 is in the open configuration, fluid and particulate matter can be sucked through the expandable isolation chamber 11 and into the evacuation conduit 22.

In further reference to FIG. 10, the suction mechanism 30 may further comprise a reservoir 32 that is used to collect the fluid and particulate matter that is drawn out of the patient through the evacuation conduit 22; the reservoir 32 being in fluid communication with the evacuation conduit 22 and the vacuum unit 31. Preferably, the vacuum unit 31 is attached to the flexible body 21 via the reservoir 32, wherein the reservoir 32 is positioned in between the evacuation conduit 22 and the vacuum unit 31 in order to prevent the vacuum unit 31 from clogging. However, it is possible for the vacuum unit 31 to be positioned in between the flexible body 21 and the reservoir 32.

In reference to FIG. 2, in the preferred embodiment of the present invention, the expandable isolation chamber 11 comprises a container base 12 and a plurality of fingers 13. The container base 12 is adjacently connected to the flexible body 21 and has an opening that is aligned with the evacuation conduit 22, wherein fluid and particulate matter can flow through the container base 12 into the evacuation conduit 22. Each of the plurality of fingers 13 is hingedly connected to the container base 12 opposite the flexible body 21, wherein each of the plurality of fingers 13 is operatively coupled to the actuation mechanism.

Figure 7:
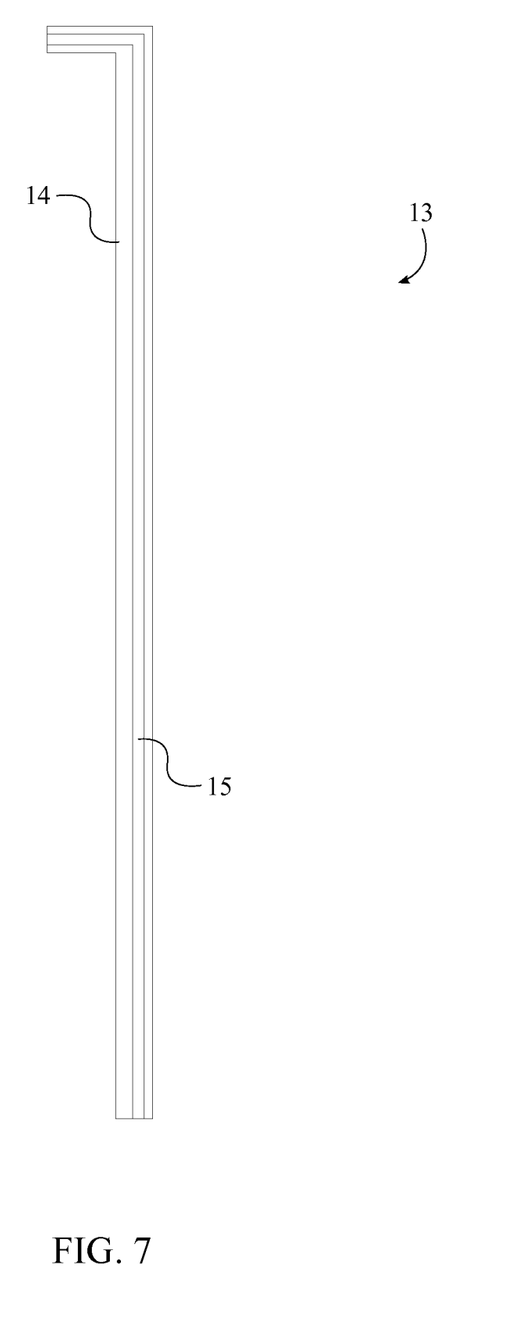
FIG. 7 is a side view of one of the plurality of fingers, wherein the gasket is perimetrically positioned about the elongated body.

In reference to FIG. 7, each of the plurality of fingers 13 comprises an elongated body 14 and a gasket 15. The elongated body 14 is L-shaped, wherein the long end of the elongated body 14 is connected to the container base 12 and the short end of the elongated body 14 is positioned opposite the container base 12. The gasket 15 is adjacently connected to the elongated body 14 and is perimetrically positioned around the elongated body 14. When in the closed configuration, each of the plurality of fingers 13 is united forming an enclosed body, wherein the gasket 15 of each of the plurality of fingers 13 hermetically seals the expandable isolation chamber 11. When in the open configuration, each of the plurality of fingers 13 is disjointed, wherein each of the plurality of fingers 13 is flared outwards in order to encompass the tissue to be removed.

Figure 5:
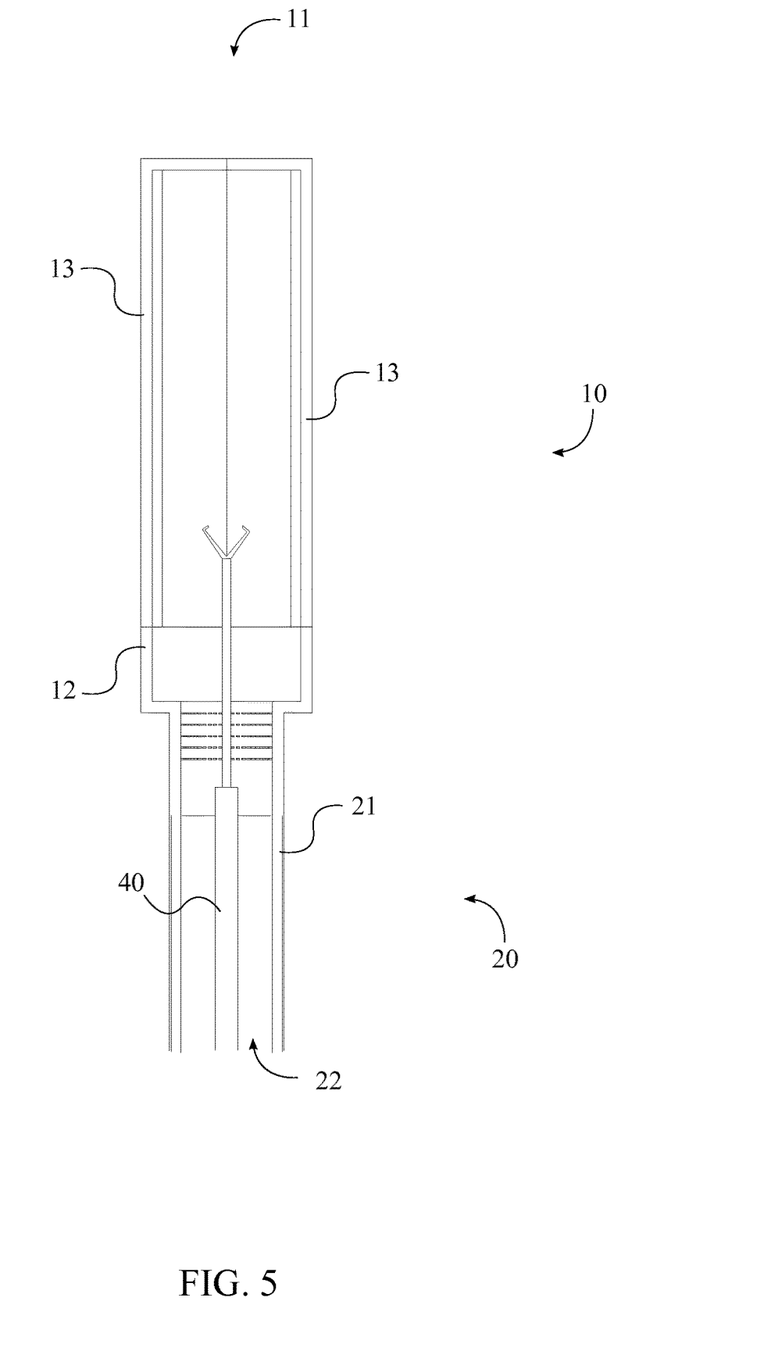
FIG. 5 is a side sectional view, wherein the morcellating mechanism is positioned through the suction tubing into the expandable isolation chamber.

In reference to FIG. 5, in other embodiments, the present invention may further comprise a morcellating mechanism 40, a gripping mechanism 50, a plurality of sensors 60, a lighting mechanism 70, a camera 80, or a cooling mechanism 90. The morcellating means traverses through the flexible body 21 into the expandable isolation chamber 11 and comprises an at least one blade; the at least one blade being positioned within the expandable isolation chamber 11. The morcellating mechanism 40 is used when the expandable isolation chamber 11 is in the closed configuration, wherein the at least one blade is used to break up particulate matter that is too large to pass through the evacuation conduit 22.

In further reference to FIG. 5, the morcellating mechanism 40 can be positioned through the evacuation conduit 22 or a subsequent conduit that longitudinally traverses through the flexible body 21 adjacent to the evacuation conduit 22. The at least one blade is terminally connected to a flexible control rod positioned through the flexible body 21 that allows the user to manipulate the at least one blade transabdominally. Alternatively, the morcellating mechanism 40 can be integrated into the expandable isolation chamber 11. In such a configuration the at least one blade can be designed to be retractable into the container base 12 when not in use so as not to unintentionally harm the patient.

Figure 6:
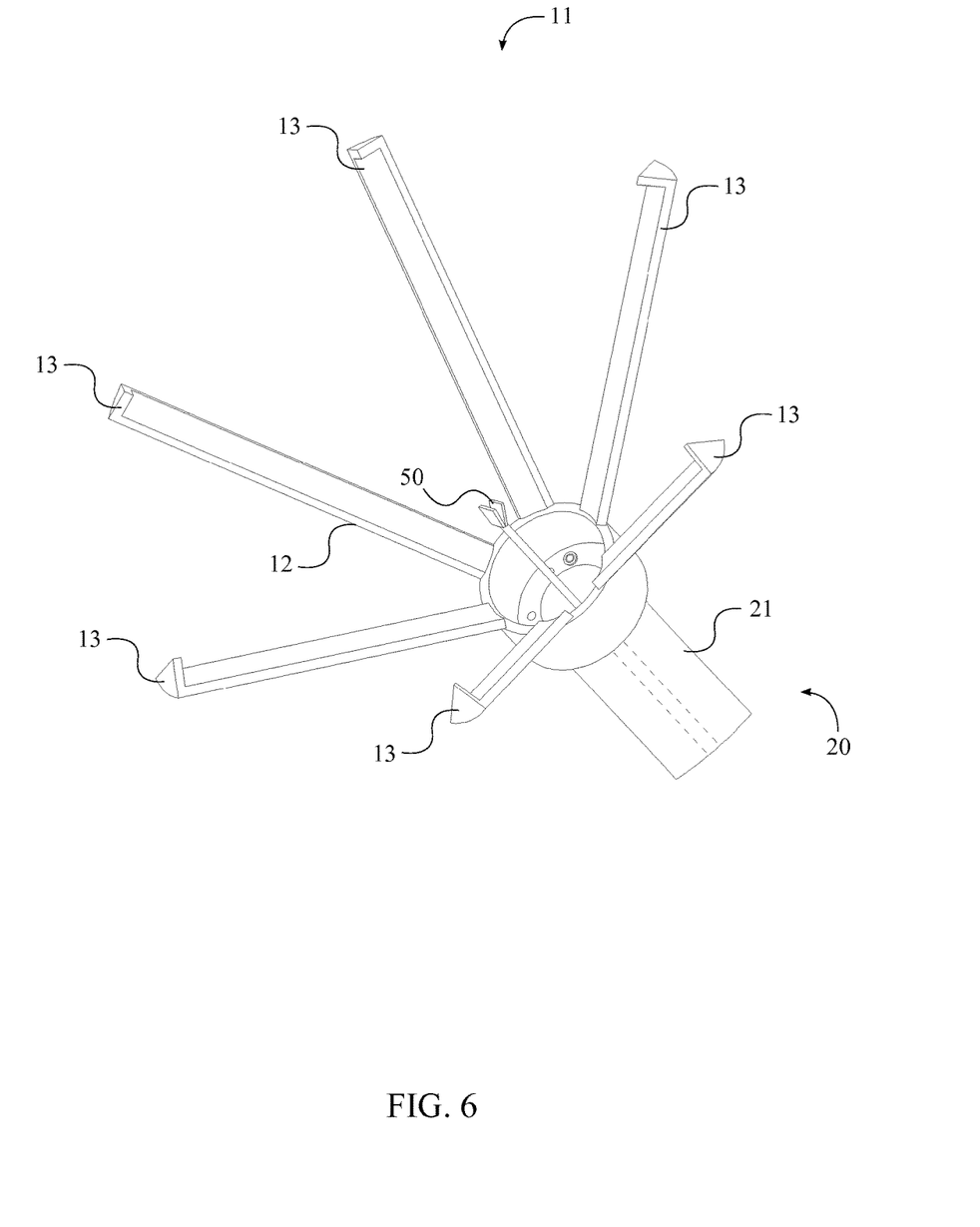
FIG. 6 is a perspective view, wherein the gripping mechanism is positioned through the suction tubing into the expandable isolation chamber.

In reference to FIG. 6, similar to the morcellating mechanism 40, the gripping mechanism 50 traverses through the flexible body 21 into the expandable isolation chamber 11; the gripping mechanism 50 being positioned through the evacuation conduit 22 or the subsequent conduit. The gripping mechanism 50 is used when the expandable isolation chamber 11 is in the open configuration, wherein the gripping mechanism 50 is used to grasp the tissue to be compacted in order to position the tissue such that the tissue will be completely enclosed by the expandable isolation chamber 11 when the expandable isolation chamber 11 is toggled to the closed configuration. Alternatively, the gripping mechanism 50 can be integrated into the expandable isolation chamber 11, wherein the gripping mechanism 50 may be designed to be retractable into the container base 12 when not in use.

Figure 4:
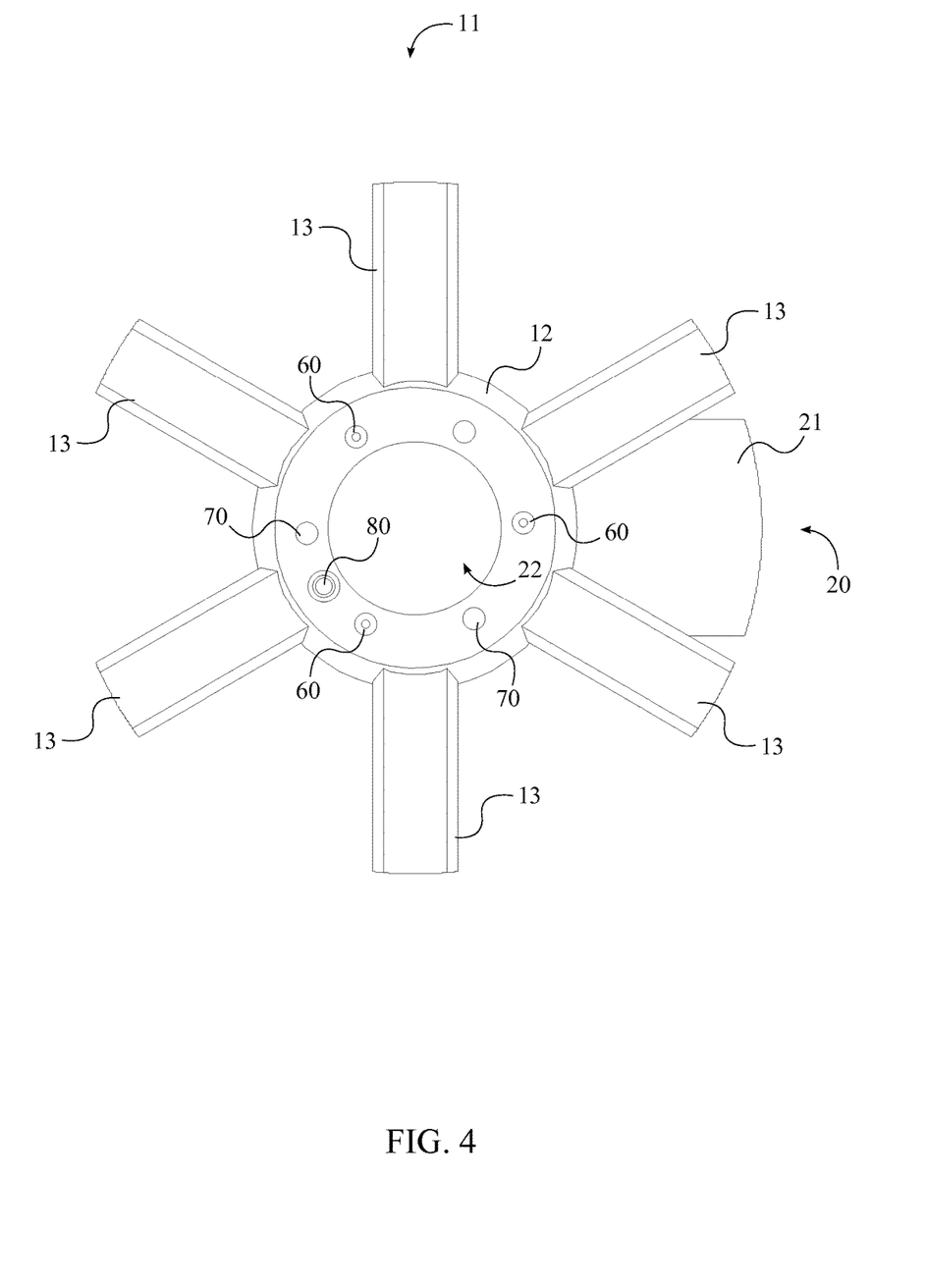
FIG. 4 is a top plan view of the compaction mechanism and the suction tubing, wherein the compaction mechanism is in the open configuration.

In reference to FIG. 4, the plurality of sensors 60 is integrated into the expandable isolation chamber 11; more specifically the container base 12. The plurality of sensors 60 allows the user to monitor various parameters while the present invention is in use and can be internally or externally positioned in relation to the expandable isolation chamber 11. The plurality of sensors 60 may include, but is not limited to, pressure sensors, temperature sensors, and sensors to detect the expanded size of the expandable isolation chamber 11. The plurality of sensors 60 can be electronically connected to a control mechanism, such as a computer, that graphically displays the readings of the plurality of sensors 60.

In order to electronically connect the plurality of sensors 60 to the control mechanism, wires are passed through the flexible body 21. More specifically, the suction tubing 20 further comprises a wiring conduit 23 that is positioned along the flexible body 21 and longitudinally traverses through the flexible body 21, as shown in FIG. 9. The wires are passed through the wiring conduit 23, wherein the wiring conduit 23 is isolated from the evacuation conduit 22 in order to keep the wires separated from the fluid and particulate matter drained through the evacuation conduit 22. Alternatively, the plurality of sensors 60 can be electronically connected to a transmitter integrated into the expandable isolation chamber 11, wherein the transmitter is able to wirelessly communicate with the control mechanism.

In reference to FIG. 4, the camera 80 is integrated into the expandable isolation chamber 11; more specifically the container base 12. The camera 80 is directed away from the suction tubing 20, allowing the user to survey the tissue and the surrounding area when the expandable isolation chamber 11 is in the open configuration. When used with the gripping mechanism 50, the camera 80 provides the user with a clear view, allowing the user to manipulate the gripping mechanism 50 and the tissue in the appropriate location. Similar to the plurality of sensors 60, the camera 80 is communicably connected to the control mechanism, either wirelessly or through a wired connection, wherein the control mechanism provides a display screen for viewing the video feed from the camera 80. Additionally, the control mechanism may be used to record the video feed that is transmitted from the camera 80.

In further reference to FIG. 4, similar to the camera 80, the lighting mechanism 70 is integrated into the expandable isolation chamber 11; more specifically the container base 12. The lighting mechanism 70 provides a source of light that is used to illuminate the internal cavity in which the expandable isolation chamber 11 is positioned, thus providing a clearer picture from the camera 80 or from a subsequent camera used in conjunction with the present invention. The lighting mechanism 70 may include a single light or a plurality of lights, and is electrically connected to the control mechanism, wherein the control mechanism can be utilized to toggle the light mechanism on and off.

The cooling mechanism 90 is integrated into the expandable isolation chamber 11 and enables the present invention to operate within an acceptable temperature range and effectively dissipate any heat that may be generated by the use of the present invention. As the tissue is compacted into a much smaller volume, the temperature within the expandable isolation chamber 11 may increase due to the increased internal pressure. This could in turn lead to the overheating of certain components or cause harm to the patient by causing internal burns.

Figure 8:
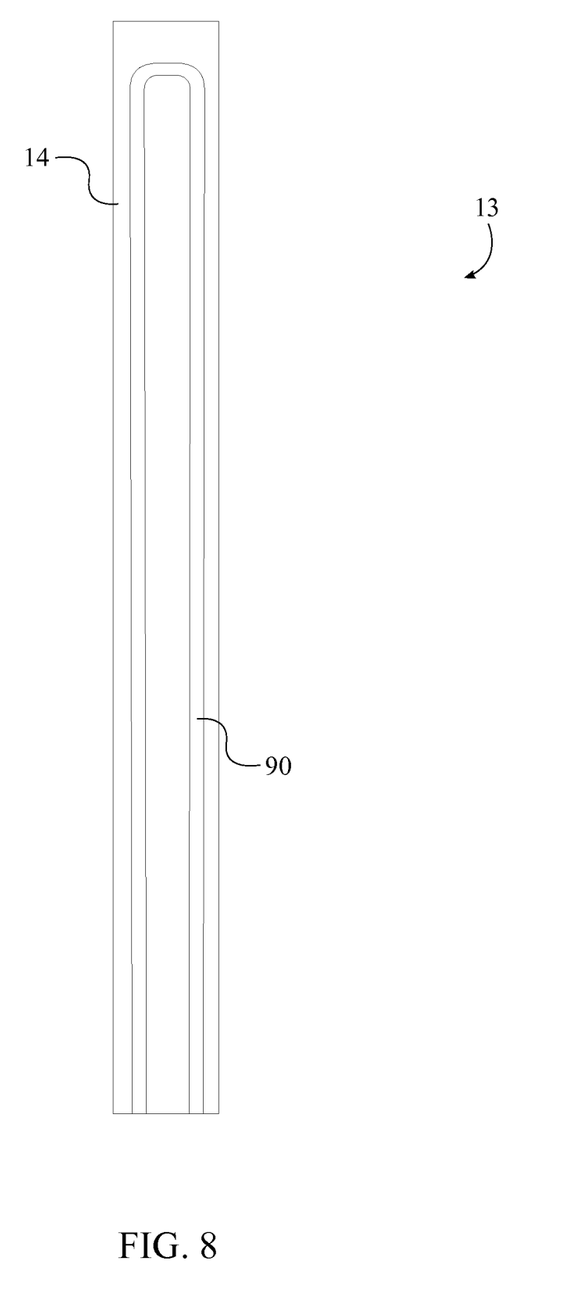
FIG. 8 is a rear sectional view of one of the plurality of fingers showing the cooling mechanism, wherein the cooling mechanism is a cooling conduit.

In reference to FIG. 8, in one embodiment, the cooling mechanism 90 comprises a plurality of cooling conduits. The plurality of cooling conduits is positioned within the expandable isolation chamber 11, both the container base 12 and the plurality of fingers 13, and allows water or another coolant to be passed through the expandable isolation chamber 11 in order to dissipate heat. The water or other coolant can be circulated to the plurality of cooling conduits by using a pump to pass the water or coolant through an inflow conduit in the suction tubing 20 and out an exit flow conduit in the suction tubing 20; both the inflow conduit and the exit flow conduit being in fluid communication with the plurality of cooling conduits.

To use the present invention, the compaction mechanism 10 is inserted trans-abdominally, trans-vaginally, etc. into the patient, wherein the suction tubing 20 is then used to manipulate the compaction mechanism 10 into the correct location. The actuation mechanism is then engaged to toggle the expandable isolation chamber 11 into the open configuration. The expandable isolation chamber 11 is then aligned with the desired tissue to be removed and the actuation mechanism is used to collapse the expandable isolation chamber 11 into the closed configuration around the tissue. As the expandable isolation chamber 11 is closed, the tissue is compacted and fully encapsulated. The suction tubing 20 and the compaction mechanism 10 are then removed from the patient.

In some embodiments of the present invention, chemicals may also be used to assist in the compaction of the tissue. The chemicals can be used to fully or partially dissolve the tissue as the tissue is encapsulated by the expandable isolation chamber 11. The chemicals may be introduced to the tissue via nozzles, a needle, or another controlled means of releasing the chemicals. Components such as the nozzles or needle can be integrated into the expandable isolation chamber 11 and may be retractable into the container base 12 to be used as needed. The control mechanism can be used to monitor and control the rate at which the chemicals are released.

Although the invention has been explained in relation to its preferred embodiment, it is to be understood that many other possible modifications and variations can be made without departing from the spirit and scope of the invention as hereinafter claimed.

What is claimed is:

1. A surgical compactor and extractor comprising:
a compaction mechanism;
a suction tubing;
a suction mechanism;
the compaction mechanism comprising an expandable isolation chamber;
the suction tubing comprising a flexible body and an evacuation conduit;
the suction mechanism comprising a vacuum unit;
the evacuation conduit being positioned along the flexible body;
the evacuation conduit longitudinally traversing through the flexible body;
the expandable isolation chamber being terminally connected to the flexible body;
the suction mechanism being terminally attached to the flexible body opposite the compaction mechanism;
the expandable isolation chamber and the vacuum unit being in fluid communication with the evacuation conduit;
the expandable isolation chamber comprising a container base and a plurality of fingers;
the container base being adjacently connected to the flexible body;
each of the plurality of fingers being hingedly connected to the container base opposite the flexible body;

the expandable isolation chamber being hermetically sealed in a closed configuration in response to the plurality of fingers being united;

the expandable isolation chamber being in an open configuration in response to the plurality of fingers being disjointed;

each of the plurality of fingers comprising an elongated body and a gasket;

the gasket being adjacently connected to the elongated body;

the gasket being perimetrically positioned around the elongated body;

a cooling mechanism;

the cooling mechanism being integrated into the expandable isolation chamber;

the cooling mechanism comprising a plurality of cooling conduits;

the plurality of cooling conduits being positioned within the expandable isolation chamber;

each of the plurality of cooling conduits being configured to allow a coolant to be passed therethrough; and a corresponding cooling conduit among the plurality of cooling conduits being disposed on a corresponding finger among the plurality of fingers.

2. The surgical compactor and extractor as claimed in claim 1 comprising:

a morcellating mechanism; and the morcellating mechanism traversing through the flexible body into the expandable isolation chamber.

3. The surgical compactor and extractor as claimed in claim 2 comprising:

the morcellating mechanism comprising an at least one blade; and the at least one blade being positioned within the expandable isolation chamber.

4. The surgical compactor and extractor as claimed in claim 1 comprising:

the suction mechanism comprising a reservoir;

the reservoir being in fluid communication with the evacuation conduit and the vacuum unit; and the reservoir being positioned in between the evacuation conduit and the vacuum unit.

5. The surgical compactor and extractor as claimed in claim 1, wherein the compaction mechanism is mechanically operated.

6. The surgical compactor and extractor as claimed in claim 1, wherein the compaction mechanism is pneumatically operated.

7. The surgical compactor and extractor as claimed in claim 1 comprising:

the suction tubing comprising a wiring conduit;

the wiring conduit being positioned along the flexible body; and the wiring conduit longitudinally traversing through the flexible body.

8. The surgical compactor and extractor as claimed in claim 1 comprising:

a plurality of sensors; and the plurality of sensors being integrated into the expandable isolation chamber.

9. The surgical compactor and extractor as claimed in claim 1 comprising:

a lighting mechanism; and the lighting mechanism being integrated into the expandable isolation chamber.

10. The surgical compactor and extractor as claimed in claim 1 comprising:

a camera; and the camera being integrated into the expandable isolation chamber.

11. The surgical compactor and extractor as claimed in claim 1 comprising:

a gripping mechanism; and the gripping mechanism traversing through the flexible body into the expandable isolation chamber.

* * * * *